(12) United States Patent
De La Torre et al.

(10) Patent No.: US 10,885,150 B2
(45) Date of Patent: Jan. 5, 2021

(54) SYSTEM AND A METHOD FOR ASSESSING PATIENT TREATMENT RISK USING OPEN DATA AND CLINICIAN INPUT

(71) Applicant: FUJITSU LIMITED, Kawasaki (JP)

(72) Inventors: Victor De La Torre, Madrid (ES); Boris Villazon-Terrazas, Madrid (ES)

(73) Assignee: FUJITSU LIMITED, Kawasaki (JP)

( * ) Notice: Subject to any disclaimer, the term of this patent is extended or adjusted under 35 U.S.C. 154(b) by 687 days.

(21) Appl. No.: 15/417,627

(22) Filed: Jan. 27, 2017

(65) Prior Publication Data

US 2017/0277857 A1    Sep. 28, 2017

(30) Foreign Application Priority Data

Mar. 24, 2016 (DE) .......................... 10 2016 205 067
Mar. 24, 2016 (GB) ................................... 1605117.9

(51) Int. Cl.
*G06F 19/00* (2018.01)
*G16H 50/30* (2018.01)

(52) U.S. Cl.
CPC ............ *G06F 19/324* (2013.01); *G06F 19/00* (2013.01); *G16H 50/30* (2018.01); *G06F 19/325* (2013.01)

(58) Field of Classification Search
CPC ...... G06F 19/324; G06F 19/00; G06F 19/325; G16H 50/30; A61B 5/7275
(Continued)

(56) References Cited

U.S. PATENT DOCUMENTS 8,751,266 B2    6/2014 Stang
9,779,214 B2 * 10/2017 Jackson ................ G06F 19/326
(Continued)

FOREIGN PATENT DOCUMENTS

CA        2832355       4/2011
CN     103914800 A      7/2014
(Continued)

OTHER PUBLICATIONS

Rizzo, G., Troncy, R. "NERD: A framework for unifying named entity recognition and disambiguation extraction tools" (2012), Proceedings of the 13th Conference of the European Chapter of the Association for Computational Linguistics, p. 73-76 (Year: 2012).*

(Continued)

*Primary Examiner* — Jason S Tiedeman
*Assistant Examiner* — Rachel F Durnin
(74) *Attorney, Agent, or Firm* — Staas & Halsey LLP

(57) ABSTRACT

A system including a healthcare risk engine to provide a healthcare risk knowledge graph from open data and knowledge data related to risk by using risk-related terms to retrieve documents from open data and by extracting the healthcare risk knowledge graph as entities from the documents and links between the entities. A patient risk graph predictor predicts risks for a patient by combining information in a Patient Clinical Object (PCO) with entities in the healthcare risk knowledge graph to produce a patient risk graph. An impact estimator estimates an impact of a treatment by taking the treatment and adjacent nodes from the healthcare risk knowledge graph to form a healthcare treatment subgraph, finding an entity and adjacent nodes in the patient risk graph to form a patient treatment subgraph, providing an impact graph by combining the patient treatment subgraph and the healthcare treatment subgraph, and retaining resultant linked nodes.

12 Claims, 12 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 2003/0130973 | A1* | 7/2003 | Sumner, II | G06F 19/3481 |
| | | | | 706/45 |
| 2007/0228721 | A1* | 10/2007 | Laposata | A61B 50/3001 |
| | | | | 283/115 |
| 2008/0215570 | A1 | 9/2008 | Maloney et al. | |
| 2009/0005650 | A1* | 1/2009 | Angell | G06Q 50/22 |
| | | | | 600/300 |
| 2012/0253139 | A1* | 10/2012 | Maman | G16H 50/20 |
| | | | | 600/300 |
| 2012/0284257 | A1* | 11/2012 | Mousses | G16B 50/00 |
| | | | | 707/722 |
| 2013/0066870 | A1* | 3/2013 | Somasundaran | G06F 19/00 |
| | | | | 707/737 |
| 2013/0144818 | A1 | 6/2013 | Jebara et al. | |
| 2013/0179181 | A1 | 7/2013 | Jackson et al. | |
| 2013/0262142 | A1* | 10/2013 | Sethumadhavan | G06F 19/00 |
| | | | | 705/3 |
| 2013/0268296 | A1 | 10/2013 | Byer et al. | |
| 2014/0095201 | A1* | 4/2014 | Farooq | G16H 50/30 |
| | | | | 705/3 |
| 2014/0344274 | A1 | 11/2014 | Kido et al. | |
| 2015/0161346 | A1 | 6/2015 | Hu et al. | |
| 2015/0193583 | A1* | 7/2015 | McNair | G16H 50/20 |
| | | | | 705/2 |
| 2015/0339778 | A1 | 11/2015 | Dunn et al. | |
| 2016/0203269 | A1* | 7/2016 | Breitenstein | G06Q 10/10 |
| | | | | 705/3 |
| 2017/0218456 | A1* | 8/2017 | Bartlett | C12Q 1/6886 |

FOREIGN PATENT DOCUMENTS

| | | |
|---|---|---|
| JP | 2013-069111 A | 4/2013 |
| JP | 2014-228907 A | 12/2014 |
| UA | 43768 U | 8/2009 |
| WO | WO-2011151500 A1 * 12/2011 | ........... G06F 16/367 |

OTHER PUBLICATIONS

Extended European Search Report dated Apr. 3, 2017 in related European Patent Application No. 16201279.3 (11 pages).
UKIPO Search Report dated Aug. 26, 2016 in corresponding Great Britain Patent Application No. GB1605117.9 (6 pages).
German Search Report dated Aug. 25, 2016 in corresponding German Patent Application No. 102016205067.2 (9 pages).
"*Graphical Modelling in Mental Health Risk Assessments*"; Obembe et al.; School of Engineering and Applied Science Aston University; Cognitive 2010: The Second International Conference on Advanced Cognitive Technologies and Applications; ISBN:978-1-61208-108-3 (6 pages).
Non-Final Office Action dated Aug. 6, 2019 in related U.S. Appl. No. 15/415,136 (24 pages).
Extended European Search Report dated Mar. 31, 2017 in related European Patent Application No. 16201282.7 (10 pages).
Extended European Search Report dated Dec. 9, 2019 in related European Patent Application No. 16201279.3 (10 pages).
Notice of Reasons for Refusal dated Apr. 7, 2020 in related Japanese Patent Application No. 2017-012894 (5 pages) (5 pages English Translation).
U.S. Appl. No. 15/415,136, filed Jan. 25, 2017, Victor De La Torre, Fujitsu Limited.
Notice of Reasons for Refusal dated Nov. 4, 2020 in related Japanese Patent Application No. 2017-012896 (6 pages) (6 pages English Translation).

* cited by examiner

SYSTEM AND A METHOD FOR ASSESSING PATIENT TREATMENT RISK USING OPEN DATA AND CLINICIAN INPUT

CROSS-REFERENCE TO RELATED APPLICATIONS

This application claims the benefits of United Kingdom Application No. 1605117.9, filed Mar. 24, 2016, in the United Kingdom Intellectual Property Office, and German Application No. 102016205067.2 filed Mar. 24, 2016 in the German Intellectual Property Office, the disclosures of which are incorporated herein by reference.

BACKGROUND

1. Field

The present invention relates to assessing healthcare of an individual or subject, usually referred to as a patient. The patient may be a human or potentially an animal, such as a specimen of a rare breed or even a pet. In many scenarios, the patient may already be suffering from a disorder, but in others the patient is currently healthy. The invention is thus widely applicable in medicine, healthcare and veterinary science.

2. Description of the Related Art

A patient's health is affected by different factors including: age, overall health condition, medicines he/she takes, recent health events like a surgery or injury, habits and life style, etc. As the patient gets older these factors contribute to the development of several health risks that could threat his/her quality of life. Well known risks are for example: the risk of developing a Coronary Heart Disease (CHD) or Type 2 Diabetes; and risk factors for risks, for example long-term cigarette smoking is a risk factor for developing chronic obstructive pulmonary disease (COPD).

In clinical practice, many protocols have been designed to estimate the risk of a patient to develop different conditions. However in most cases the health risks for a given patient are represented as a plain list, whereas the truth is that these risks are interconnected. The links between the different risks can be established at different levels. For example, the risks include the genetic background of the patient, the adverse effects of the medicines, the life style, etc.

Understanding what risks are affecting a given patient is fundamental for a clinician because he/she can decide the best treatment to apply. Importantly, since treatment by itself can be the cause of the development of a new risk, it can be useful for the clinicians to understand the associated risks for the patient after applying a treatment. Incidentally, clinicians could include, for example, nurses, doctors, dentists, healthcare practitioners and veterinary practitioners.

In summary, the inventors have come to the realisation that, within the healthcare domain:
- there are no standards for representing health risks, in the same way as there are standards for diseases, e.g., ICD9 and ICD10 (The ninth and tenth revisions of the International Classification of Diseases); there are only plain lists of risks and they are specific to a particular medical institution or area;
- there are no approaches that estimate the potential risk of a patient after applying a particular treatment;

SUMMARY

According to an embodiment of a first aspect of the invention, there is provided a system for assessing patient treatment risk using open data and clinician input, the system comprising: a healthcare knowledge data input to receive open data and an expert knowledge input to accept input of clinician knowledge relating to risk; a healthcare risk engine to provide a healthcare risk knowledge graph from the open data and clinician input by using clinician input of risk-related terms to retrieve relevant documents from the open data and by extracting the healthcare risk knowledge graph as entities from the documents corresponding to the clinician's terms, as well as the links between the entities; a patient risk graph prediction module to predict risks for a specific patient by combining information in a Patient Clinical Object, PCO, with entities in the healthcare risk knowledge graph to produce a patient risk graph; and an impact estimator module to estimate the impact of a potential specific treatment by taking the specific treatment and adjacent nodes from the healthcare risk knowledge graph to form a healthcare treatment subgraph and finding one or more corresponding entities and (their) adjacent nodes in the patient risk graph to form a patient treatment subgraph, and providing an impact graph by combining the patient treatment subgraph and the healthcare treatment subgraph and retaining the resultant linked nodes as the impact graph.

The patient risk graph provides specific information for a patient, in a way that is easily comprehensible and can help a clinician or other user to foresee risks based not only on the patient's own data, but also on freely available databases, The impact estimator module then uses this patient-specific information in combination with the open data in the healthcare risks knowledge graph to estimate risks which are not currently available from the patient's own data, but are associated with the treatment that the patient is receiving.

Invention embodiments use a specific potential treatment and adjacent nodes in the healthcare risk knowledge graph to form a patient treatment subgraph, and find at least one corresponding entity (i.e. that corresponds to one or more nodes in the treatment subgraph) and adjacent nodes from the patient risk graph. For this correspondence, an exact match of the terms may be required or a threshold level of similarity may suffice.

The patient's own data is initially in the form of the PCO, which is an aggregation of clinical entities that encapsulates items of information about a given patient. Preferably the PCO contains historical clinical information as a graph centred on the patient, with information about the patient linked to the patient by categories, such as any of diagnosis, symptom, treatment, hospital visit and prescription. The PCO may be input or already available in the system.

The clinician's terms can include terms related to risks in the form of potential diseases, terms related to risk factors that increase the likelihood of disease and terms related to treatments of a medical condition.

In one embodiment, the health risk engine can include the following components: a risk related terms collector to accept input of terms by a clinician, the clinician's terms including terms related to risks in the form of potential diseases, terms related to risk factors that increase the likelihood of disease and terms related to treatments of a medical condition; a medical entity reconciliator, to standardise and expand the clinicians' terms to include synonyms and equivalent terms using a standardised vocabulary of terms; a topic detector and tagger, to retrieve a set of documents linked to the expanded terms from a medical document database; a named entity recognition, resolution and disambiguation, NERD, module to extract entities from the set of document each with a score and each aligned to the standardised vocabulary; and a relation extractor to score relations between the entities based on the co-occurrence of two entities in documents, and potentially also on the context in the retrieved set of documents; wherein the healthcare risks extraction system is arranged to generate a risk knowledge graph storing the entities and their scored relations.

The system may further comprises a knowledge graph curator, to display the risk knowledge graph and to accept clinician input to manually curate the generated graph.

The risk related terms collector may be arranged to accept the terms as a list (or lists) of terms per category of risk, risk factor and treatment. This can be by input of plain text, and the clinician (or clinicians) does not need to enter any other information, such as links between the terms.

The topic detector (and tagger) can be arranged to take into account the provenance of the documents, for example which journal they came from, the journal date etc. This provenance can be taken into account potentially for scoring and other purposes later. In this case, the risk knowledge graph can also store the provenance of the entities. This can provide that extra information to the user.

The risk related terms collector (or another component of the system) may be arranged to accept annotations by the clinician of the standardised vocabulary of terms, the annotations labelling vocabulary in categories of risks, risk factors and treatments.

The topic detector and tagger may be arranged to tag the documents according to categories of risks, risk factors and treatments and additionally according to the main topic of the document, which is not necessarily a risk, risk factor or treatment. This information may be available due to the annotations entered as explained above. This tagging process is important because it can identify the main topic of the documents, and then the system can create relations between this primary topic and the named entities of the document. This is one particular way to deal with the context.

In some embodiments, the NERD module scores each entity to reflect the accuracy of a match between the standardised vocabulary term and the corresponding term or terms in the retrieved linked documents.

In a simple embodiment, the patient risk graph prediction module can predict risks for a specific patient by matching an item of information from the PCO with a corresponding entity (or more than one entity) in the healthcare risk knowledge graph, and extracting nodes around the entity to form the patient risk graph. For example an exact match may be required or a threshold level of similarity.

Other embodiments use different strategies for prediction, each giving an individual patient risk subgraph and then combine the subgraphs. In one embodiment the patient risk graph prediction module is a meta-predictor which is arranged to use the PCO and healthcare risk knowledge graph in two or more predictors. The predictors can include: a diagnosis-based predictor to provide a patient risk subgraph based on previous diagnoses, a drug-based predictor to provide a patient risk subgraph based on previous drugs taken by the patient, a symptom-based predictor to provide a patient risk subgraph based on previous symptoms of the patient and a treatment-based predictor to provide a patient risk subgraph based on the treatments the patient is receiving. In this case the meta diagnosis prediction module can include a meta predictor to makes predictions by organizing and processing the patient risk subgraphs produced by the individual predictors into a patient risk graph.

Each patient risk subgraph constructed by a predictor includes any entities in the healthcare risk knowledge graph which match the item of information. For example an exact match may be required or a threshold level of similarity. One or more entities which neighbour the matching entities (preferably all those within 2 steps of the matching entity) and the entities on a shortest path between the matching entities may also be included.

Each predictor can be given a weighting based on an accuracy of performance measure. Such a weighting can then be used to determine the maximum number of entities in the subgraph which is retained in the patient risk graph.

The links between the entities may include a score to show the strength of the relation, and additionally each entity in the healthcare risk knowledge graph can include a score to reflect how closely the entity corresponds to the clinician's term. One or both of these scores can be taken across to the patient risk graph.

The entity score can also be used in the meta predictor. For example, the meta predictor selects from the entities included by the predictors one or more which is present in the highest number of predictors and/or has the highest cumulative score as the patient risk graph.

The impact estimator module can use any suitable number of entities (nodes) in the patient risk graph to form the patient treatment subgraph, and any suitable selection means. In one example, the impact estimator module takes any nodes matching the healthcare treatment subgraph and nodes within 1 or 2 or 3 links from the matching node(s) to form the patient treatment subgraph.

The impact estimator module can use any suitable number of entities (nodes) in the healthcare risk graph to form the healthcare treatment subgraph, and any suitable selection means. For example, the impact estimator module can take the entity or node for the specific treatment, and can include further nodes including at least one entity in the risk or risk factor category to form the healthcare treatment subgraph.

In a more specific example, the impact estimator module takes the entity for the specific treatment, and includes all the risks and/or risk factors within 2 or 3 links from the entity to form the healthcare treatment subgraph.

In this case, the impact estimator module can also include 2 or 3 further links starting from each risk to form the healthcare treatment subgraph.

The system may further comprise a translation module to accept a term in one language and translate it into the equivalent in the language of the standardised vocabulary.

According to an embodiment of a second aspect of the invention, there is provided a computer-implemented method for assessing patient risk using open data and clinician input, the method comprising: receiving open data and clinician knowledge relating to risk; providing a healthcare risk knowledge graph from the open data and clinician input by using clinician input of risk-related terms to retrieve relevant documents from the open data and by extracting the healthcare risk knowledge graph as entities from the documents corresponding to the clinician's terms, as well as the links between the entities; predicting risks for a specific patient by combining information in a Patient Clinical Object, PCO, with entities in the healthcare risk knowledge graph to produce a patient risk graph; and estimating the impact of a specific potential treatment by taking the specific treatment and adjacent nodes from the healthcare risk knowledge graph to form a healthcare treatment subgraph and finding a corresponding entity and adjacent nodes in the patient risk graph to form a patient treatment subgraph, and providing an impact graph by combining the patient treatment subgraph and the healthcare treatment subgraph and retaining the resultant linked nodes as the impact graph.

According to an embodiment of a third aspect of the invention, there is provided a computer program which when executed on a computer carries out the method described above.

A method or computer program according to preferred embodiments of the present invention can comprise any combination of the previous apparatus aspects, but without restriction as to the specific parts of the system involved. Methods or computer programs according to these further embodiments can be described as computer-implemented in that they require processing and memory capability.

The apparatus according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the system according to any of the preceding system definitions or any combination thereof.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface.

The invention can be implemented in digital electronic circuitry, or in computer hardware, firmware, software, or in combinations of them. The invention can be implemented as a computer program or computer program product, i.e., a computer program tangibly embodied in a non-transitory information carrier, e.g., in a machine-readable storage device, or in a propagated signal, for execution by, or to control the operation of, one or more hardware modules. A computer program can be in the form of a stand-alone program, a computer program portion or more than one computer program and can be written in any form of programming language, including compiled or interpreted languages, and it can be deployed in any form, including as a stand-alone program or as a module, component, subroutine, or other unit suitable for use in a data processing environment. A computer program can be deployed to be executed on one module or on multiple modules at one site or distributed across multiple sites and interconnected by a communication network.

Method steps of the invention can be performed by one or more programmable processors executing a computer program to perform functions of the invention by operating on input data and generating output. Apparatus of the invention can be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The invention is described in terms of particular embodiments. Other embodiments are within the scope of the following claims. For example, the steps of the invention can be performed in a different order and still achieve desirable results. Multiple test script versions can be edited and invoked as a unit without using object-oriented programming technology; for example, the elements of a script object can be organized in a structured database or a file system, and the operations described as being performed by the script object can be performed by a test control program.

Elements of the invention have been described using the terms "module" and "unit" and functional definitions. The skilled person will appreciate that such terms and their equivalents may refer to parts of the system that are spatially separate but combine to serve the function defined. Equally, the same physical parts of the system may provide two or more of the functions defined.

For example, separately defined means may be implemented using the same memory and/or processor as appropriate.

BRIEF DESCRIPTION OF THE DRAWINGS

Preferred features of the present invention will now be described, purely by way of example, with references to the accompanying drawings, in which.

DETAILED DESCRIPTION

Figure 1:
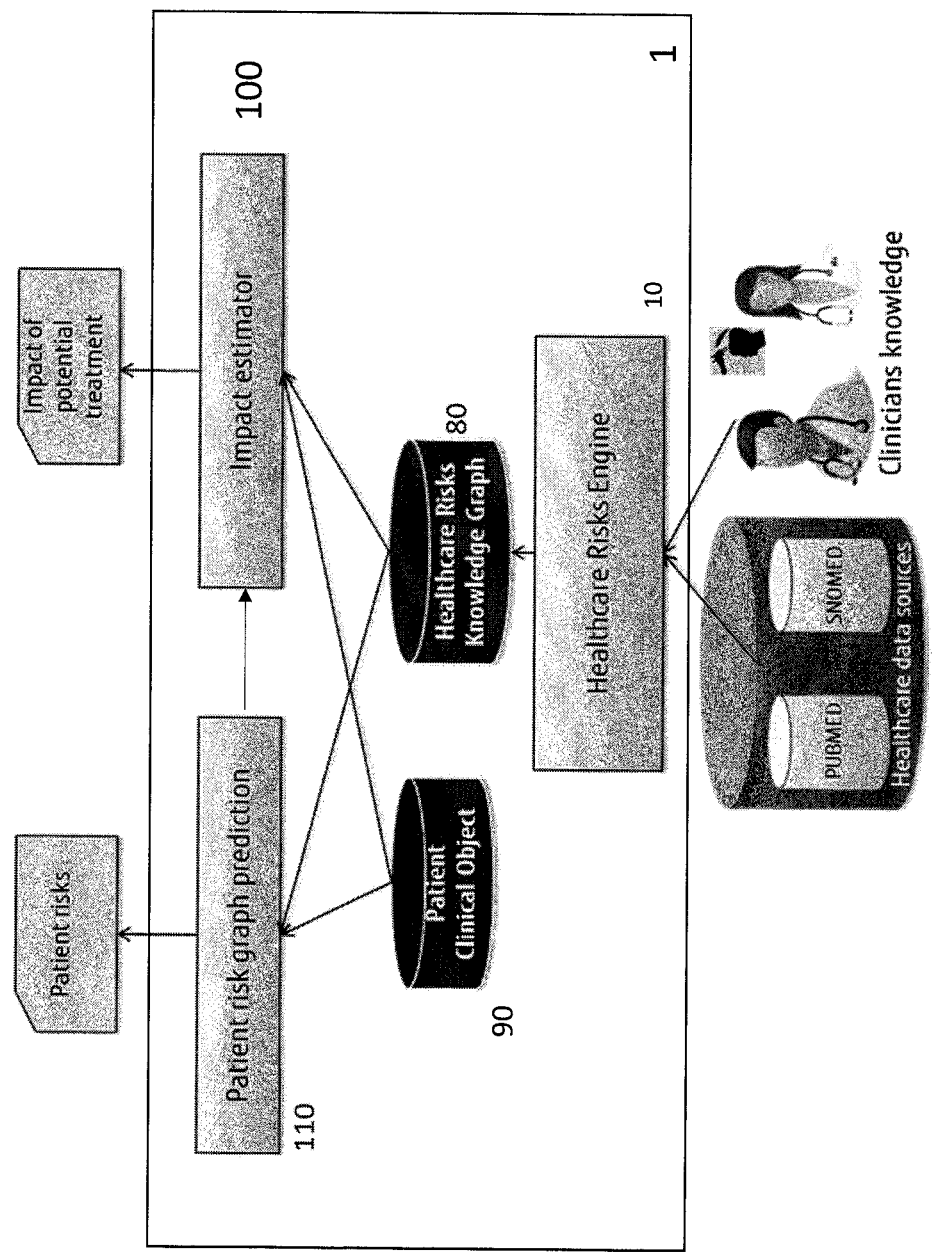
FIG. 1 is a block diagram of components in an embodiment of the invention.

Embodiments of the invention may aim:
to create a network of Health Risks, represented as a Knowledge Graph, extracted from the literature and public data sources together with the clinicians' expertise on risk assessment;
to develop a mechanism that identifies the associated risks for a particular patient given his/her clinical history information, such as, diagnoses, drugs, and symptoms; enrich the patient clinical history with his/her risk information; and
to develop a mechanism that identifies the associated risks of a patient after applying a particular treatment.

Precision medicine is a medical model that proposes the customisation of healthcare, tailored to the individual patient/subject. This is an emerging approach for disease diagnosis, treatment and prevention that takes into account individual variability in genes, physiology, anatomy, environment, and lifestyle. In this context invention embodiments support the individual variability of the patients by including health risks, along with their associated treatments, diagnosis, and drugs.

The following definitions are used in this document:

Health risk (or simply risk): a disease or condition precursor associated with a higher than average morbidity or mortality rate. Disease precursors include demographic variables, certain individual behaviours, familial and individual histories, and certain physiological changes.

Health risk factor: a condition, behaviour, or other factor that increases risk, e.g., depression is a risk factor in suicide.

Medical treatment: the management and care of a patient, including for example in the mental health area, nursing, psychological intervention and specialist mental health rehabilitation. This term may also include "alternative" medical treatments and medication which may be prescribed, if so wished, for example, homeopathic/hypnosis/acupuncture treatment.

Diagnosis: the process of determining by examination the nature and circumstance of a disease or condition from its signs and symptoms Drugs: medicaments that treat or prevent or alleviate the symptoms of a disease.

As far as the inventors are aware, there is no standard resource for dealing with health risks, there are only ad-hoc resources such as plain lists, or matrices within medical institutions and for specific areas.

In summary:
there are no standards for representing health risks, in the same way as there are standards for diseases, e.g., ICD9; there are only plain lists of risks and they are specific to a particular medical institution or area;
there is a lack of methods and tools that exploits the information of the healthcare risks and their association to patient clinical data;
there are no approaches that estimate the potential risks of a patient after applying a particular treatment Invention embodiments create a network of medical risks of a given patient and evaluate the potential impact of a treatment for such patient.

A detailed embodiment might consist of three main modules
A module for the creation of Health Risks Knowledge Base/Graph based on information extracted from the literature and public data sources together with the clinicians' expertise on risk assessment.
A module that predicts for a given patient a health risks subgraph that is affected
An impact estimator module which estimates the impact of a potential treatment in the patient risk graph.

The system 1 according to one invention embodiment includes a Health Risks Knowledge Graph builder module 10, based on information obtained from literature, and available standards which creates a knowledge graph 80; a patient risk graph prediction module 110, which predicts the risks for a given patient, and an impact estimator 100, which uses the predicted patient-specific risks to estimate the impact of a potential treatment. The patient risk graph prediction module may form part of the impact estimator. In this case, the patient risk graph prediction may be an interim product and not necessarily directly output to the user, so that the system outputs the potential impact of the treatment only (for example using a GUI).

It is worth mentioning that the solution in this embodiment also relies on a "Patient Clinical Object" (PCO) 90 which is defined as a semantically rich aggregation of clinical entities that encapsulates information about a given patient. This PCO contains historical clinical information, such as information about the patient and its clinical data, diagnoses, and drugs.

FIG. 1 shows the main components of the system 1 for health risk assessment. There is a healthcare knowledge data input to receive open data and an expert knowledge input to accept input of form one or more clinicians relating to risk. The clinician knowledge is input by people directly, and can be grouped into risks, risk factors and treatments. The open data may be from healthcare data sources such as PUBMED and SNOMED, as explained in more detail below.

A healthcare risk engine 10 is used to provide a healthcare risk knowledge graph from the open data and clinician input. This uses the human knowledge of (a) clinician(s), who inputs risk-related terms to retrieve relevant documents from the open data. The healthcare risk knowledge graph is extracted as entities (standardised terms, but also including the clinician's original terms) from the documents corresponding to the clinician's terms, as well as the links between the entities.

A patient risk graph prediction module 110 predicts risks for a specific patient by combining information in a Patient Clinical Object, PCO, 90 with entities in the healthcare risk knowledge graph to produce a patient risk graph.

An impact estimator module 100 estimates the impact of a specific potential treatment by taking the specific treatment and adjacent nodes from the healthcare risk knowledge graph to form a healthcare treatment subgraph and finding a corresponding entity and adjacent nodes in the patient risk graph to form a patient treatment subgraph and providing an impact graph by combining the patient treatment subgraph and the healthcare treatment subgraph and retaining some or all of the resultant linked nodes as the impact graph.

Figure 2:
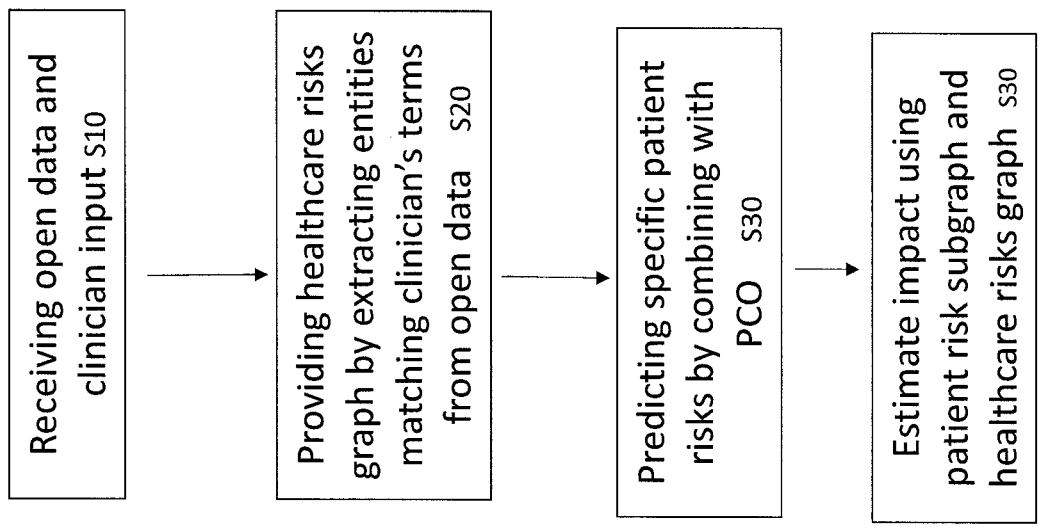
FIG. 2 is a flow chart of a method in a general embodiment.

FIG. 2 illustrates a corresponding method, including receiving, S10, open data and clinician knowledge relating to risk; providing, S20, a healthcare risk knowledge graph from the open data and clinician input by using clinician input of risk-related terms to retrieve relevant documents from the open data and by extracting the healthcare risk knowledge graph as entities from the documents corresponding to the clinician's terms, as well as the links between the entities; and predicting, S30, risks for a specific patient by combining information in a Patient Clinical Object, PCO, with entities in the healthcare risk knowledge graph to produce a patient risk graph. Finally step S30 involves estimating the impact of a specific potential treatment by taking the specific treatment and adjacent nodes from the healthcare risk knowledge graph to form a healthcare treatment subgraph and finding a corresponding entity and adjacent nodes in the patient risk graph to form a patient treatment subgraph and providing an impact graph by combining the patient treatment subgraph and the healthcare treatment subgraph and retaining the resultant linked nodes as the impact graph.

The specific modules of the system are described in more detail below.

Health Risk Engine 10

This module captures the evidence based on data derived from literature and public data sources, such as PUBMED (PUBMED is a service of the US National Library of Medicine (NLM) and provides free access to the NLM database of nursing, veterinary, healthcare, medical and scientific articles) and SNOMED (Systemized Nomenclature of Medicine).

One underlying concept is that the data used covers a wide range of different risks and risk factors: invention embodiments are not limited to a certain area of medicine. For example SNOMED CT (clinical terms) is a standardised multilingual vocabulary which is generally applicable across medical and health care areas. PUBMED is also as wide-ranging as the US NLM and thus generally applicable.

Figure 3:
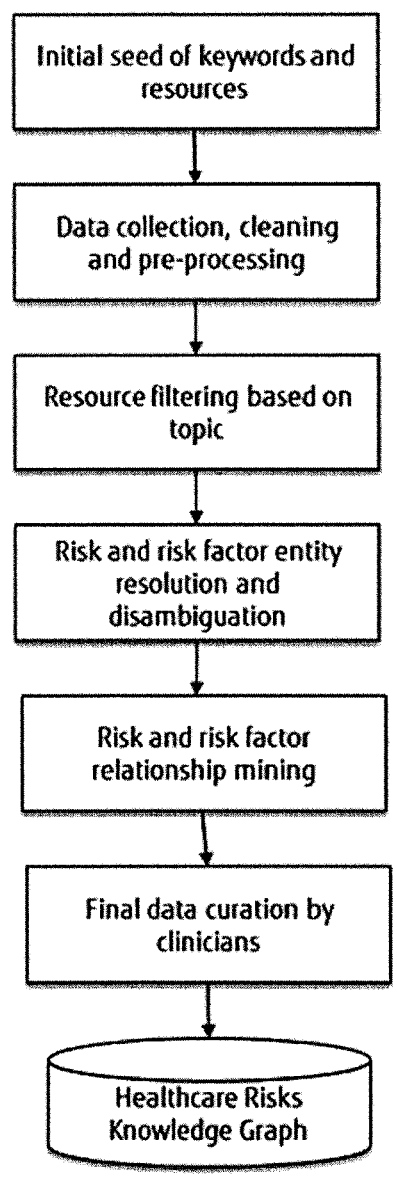
FIG. 3 is a flowchart of a method in a healthcare risks engine.

The process carried out by the module is shown in FIG. 3. It starts with an initial seed of keywords provided by the clinicians. With this seed the task of data collection, cleaning and pre-processing is performed. This task consists of searching for risk related information on available open datasets. Once we have the initial set of risk related terms the engine filters those terms according to a particular topic. The next task consists of performing some text mining over the initial set of extracted terms to get the risk and risks factors along with the relationships among them. Finally, the system allows clinicians to carry out a manual curation task to identify and find possible mistakes and inconsistencies in the graph.

Figure 4:
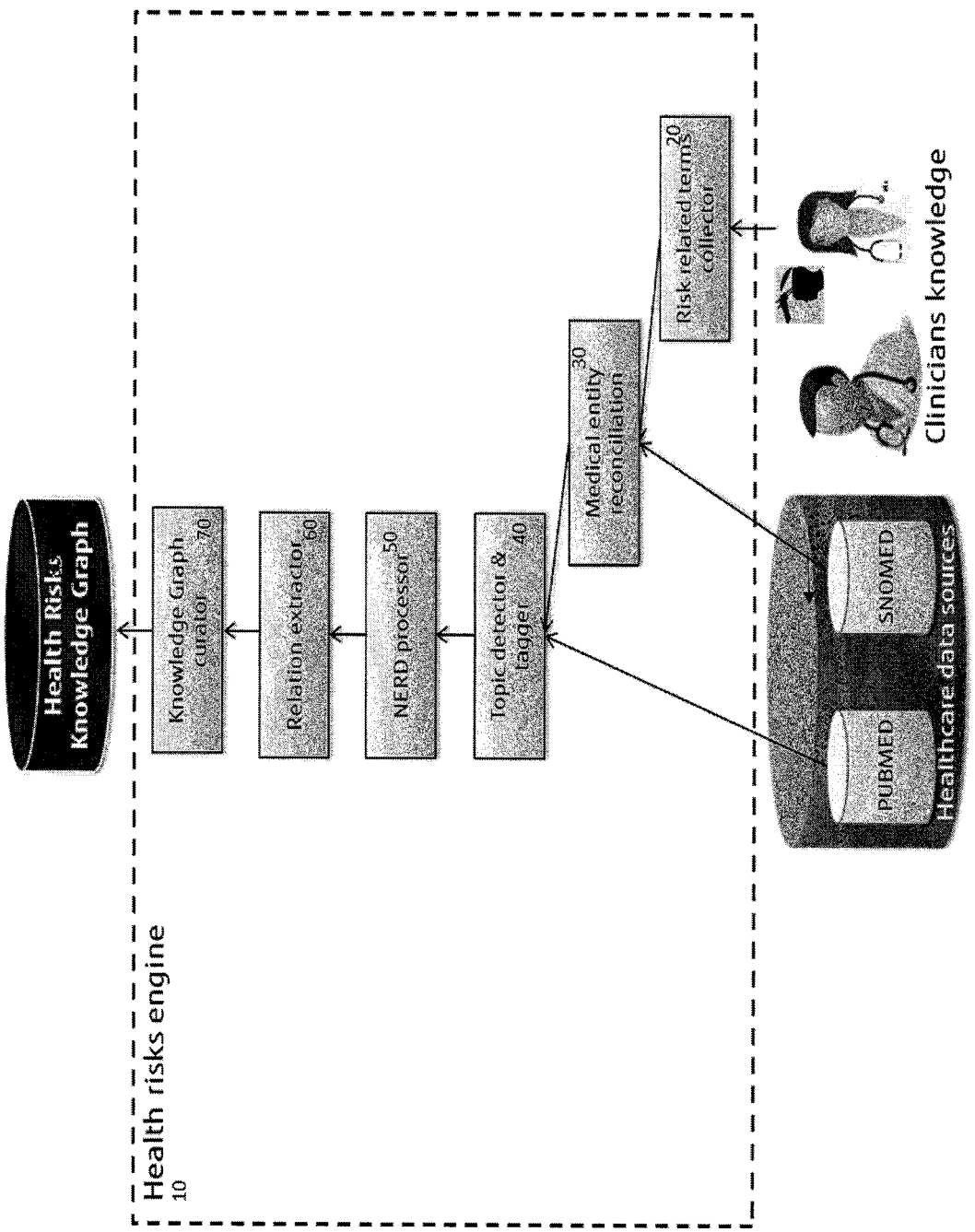
FIG. 4 is a block diagram of a system for providing a health risk knowledge graph.

FIG. 4 shows one example of a specific healthcare risk engine which accepts inputs from clinicians and is connected to open data in the form of a standardised vocabulary of terms and a library of documents from the healthcare domain, nursing, veterinary, healthcare, medical and scientific articles. Individual modules are explained further below.

A risk related terms collector 20 accepts input of seed terms by a clinician (or from a group of clinicians). These clinician's terms include terms related to risks in the form of potential diseases or conditions, terms related to risk factors that increase the likelihood of disease and terms related to treatments of a medical condition.

For data collection, cleaning and pre-processing, a medical entity reconciliator 30 can be used to standardise and expand the clinicians' terms to include synonyms and equivalent terms using a standardised vocabulary of terms. For example the SNOMED ontologies may be used, as explained in more detail later.

A topic detector 40 is used to filter resources by retrieving a set of documents linked to the expanded terms from a searchable medical document database (such as PUBMED). Essentially, this component compares the documents contents (for example their abstracts) with the standardised terms and selects the documents which include exactly those terms or close matches to those terms. It also tags the documents with their main topic(s).

A named entity recognition, resolution and disambiguation, NERD, module 50 extracts entities from the set of document each with a score and each aligned to the standardised vocabulary. That is, the entity may be taken from the SNOMED vocabulary, for example, but is matched to the document content.

A relation extractor 60 scores relations between the entities based on the co-occurrence of two entities in documents in the retrieved set of documents. For example, this can use known co-occurrence metrics.

The healthcare risks extraction system is arranged to generate a risk knowledge graph 80 storing the entities and their scored relations. The graph is generated by the parts explained above. The graph can then be displayed to the user (who might for instance be another clinician). For example the user might enter a term, such as a risk, risk factor or treatment and receive a subgraph of the linked terms and the strength of the link, based on the knowledge implicitly stored in the PUBMED library. However, the healthcare risk knowledge graphs is combined with a PCO in invention embodiments, to provide individual risk information.

PCO 90

Figure 5:
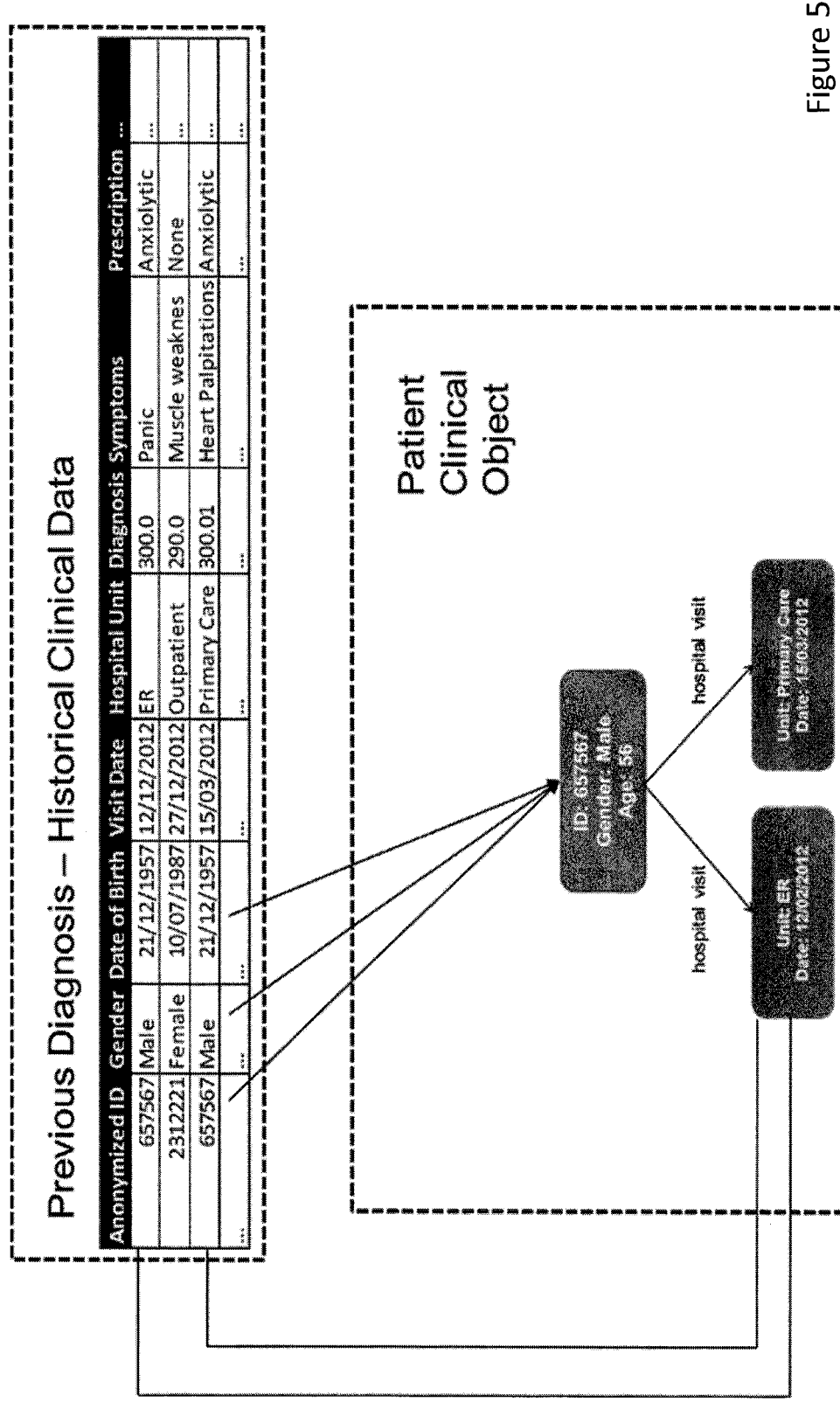
FIG. 5 is a block diagram illustrating production of a PCO

An example of a PCO in construction is shown in FIG. 5. The PCO is, for example, provided from historical clinical data as a graph centred on the patient, with information about the patient linked to the patient by categories, such as any of diagnosis, symptom, treatment, hospital visit and prescription. The historical clinical data may be provided, for instance from hospital records, or health authority records. A PCO enricher may be provided in the data and knowledge acquisition system, to compare the PCO with a biomedical knowledge graph to equate PCO parts with standard vocabulary and to annotate entities in the PCO with corresponding concepts/information from the biomedical knowledge graph.

Patient Risk Graph Prediction 110

The patient risk prediction module can be a meta-predictor, also known as hybrid/combined predictor, that makes predictions by organizing and processing the predictions produced by several predictors. The individual predictors may take the information for the relevant features from the Patient Clinical Object, and the Healthcare Risks Knowledge graph.

The individual predictors are

Predictor based on previous diagnoses. In this case the prediction is made by checking and reviewing the previous diagnoses of the patient.

Predictor based on the drugs the patient was taking.

Predictor based on the symptoms of the patient.

Predictor based on the treatments the patient is receiving.

Figure 6:
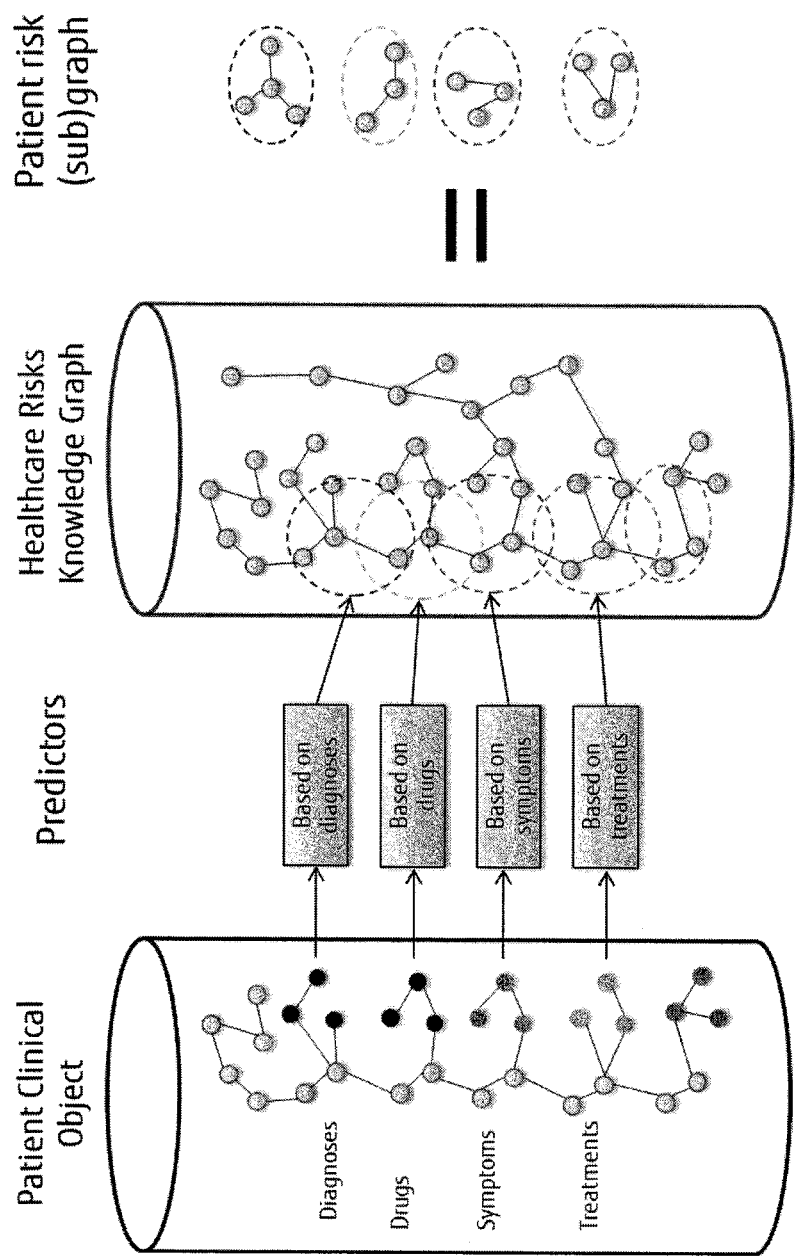
FIG. 6 is a block diagram illustrating modules in a predictor.

FIG. 6 depicts each one of the predictors and their relation with the Patient Clinical Object, Healthcare Risks Knowledge graph and the output, which is the patient risk sub graph prediction. This prediction indicates which risks are valid for a particular patient. Nodes of the subgraph can include risks, risk factors and treatments.

Each predictor uses items of information (terms) and potentially surrounding terms (which can be used as context) found in the PCO and searches for matching entities (also terms, which form nodes in the graph) in the healthcare risks knowledge graph. It then expands the subgraph around the corresponding terms to include further entities. For example, if there are several corresponding terms, the subgraph may be expanded to include all the nodes in the shortest path between the corresponding terms and the 1, 2 or 3 adjacent terms to each corresponding term.

Once we have the outputs of the individual predictors, a meta predictor component combines the individual predictors in order to offer better predicting performance and to see which terms (nodes) to retain in the patient subgraph. To weight this combination, the component adjusts weights to each one of the predictors, for example using the following equation $$R_j = W_d P_d + W_{dr} P_{dr} + W_s P_s + W_t P_t$$

Where $R_j$ is the predicted patient risks (sub) graph $W_d$ is the assigned weight to the predictor based on previous diagnosis $P_d$ is the prediction based on previous diagnosis $W_{dr}$ is the assigned weight to the predictor based on drugs the patient was taking $P_{dr}$ is the prediction based on drugs the patient was taking $W_s$ is the assigned weight to the predictor based on symptoms of the patient $P_s$ is the prediction based on symptoms of the patient.

$W_t$ is the assigned weight to the predictor based on treatments of the patient $P_t$ is the prediction based on treatments of the patient The component takes a sample from the population of patients and creates a training dataset. The goal of the component is to build an algorithm that automatically applies the predictors, and makes a best guess or estimate the patient risk subgraph.

A detailed example of meta-prediction follows, using the equation as set out previously.

Basically, each predictor outputs a set of risks, risk factors and treatments (entities) each ranked based on the score of that entity in the healthcare risk graph.

The weight for each predictor represents how accurate its risk assessment is. Each weight then represents the number of entities we consider for each predictor. The meta predictor outputs the intersection of the repeated entities of the individual predictors.

For example, and using numbers for the entities, the predictor based on previous diagnoses may have the following output:

| D | Score |
|---|---|
| 300.00 | 0.7 |
| 290.0 | 0.5 |
| 300.01 | 0.5 |
| 290.01 | 0.4 |

And a weight of 2 represents that we only consider the first two risks (*) for that predictor:

| D | Score |
|---|---|
| *300.00 | *0.7 |
| *290.0 | *0.5 |
| 300.01 | 0.5 |
| 290.01 | 0.4 |

Let us suppose we have the following example $$R_j = W_d P_d + W_{dr} P_{dr} + W_s P_s + W_t P_t$$

And replacing the results of the predictors:

| 2 | | +3 | | +4 | | +2 | |
|---|---|---|---|---|---|---|---|
| D | Score | D | Score | D | Score | D | Score |
| *300.0 | *0.7 | *290.1 | *0.8 | *290.0 | *0.7 | *291.0 | *0.7 |
| *290.0 | *0.5 | *290.0 | *0.8 | *293.0 | *0.6 | *290.0 | *0.6 |
| 300.01 | 0.5 | *300.01 | *0.7 | *301.01 | *0.6 | 301.01 | 0.5 |
| 290.01 | 0.4 | 291.01 | 0.7 | *296.01 | *0.5 | 296.01 | 0.4 |
|  |  | 292.0 | 0.6 | 297.0 | 0.4 | 297.0 | 0.4 |
|  |  |  |  | 293.1 | 0.4 | 293.1 | 0.4 |

Next, the meta predictor checks which entities are present in all the individual predictors and selects the ones with a high score (above a threshold) in terms of the largest cumulative score and/or largest number of times they appears. These nodes are included in the patient risk graph.

The meta predictor, in order to calculate the weights, is trained in advance on a pre-defined set of training examples, which then facilitate its ability to reach an accurate diagnosis when given new patient data.

The subgraph can be used in many flexible ways and contains significantly more information than a simple list of risks.

Figure 7:
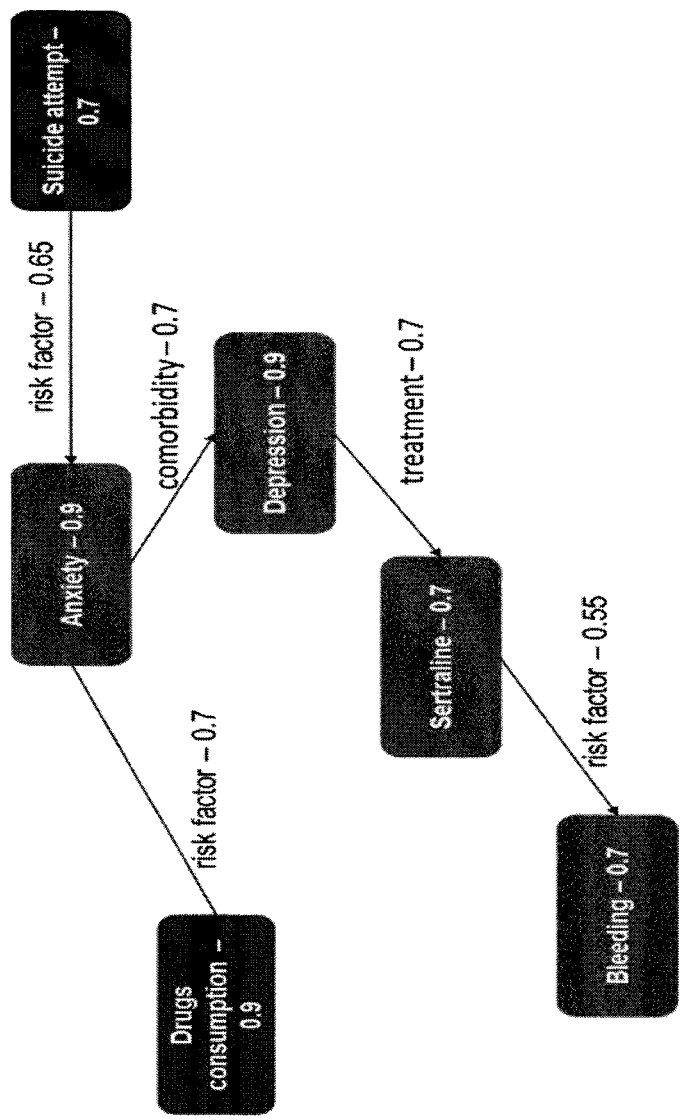
FIG. 7 is an illustration of an excerpt from a health risk knowledge graph.

FIG. 7 shows an excerpt of a risk knowledge graph showing how biomedical related information is encoded in a graph. The graph database contains information about diagnoses (or risks), drugs, treatments, and symptoms, and the relations between them. For example the weights on the links between the terms show how strongly they are related using the co-occurrence metrics mentioned previously.

In this particular example the graph identifies the relation between Anxiety and Depression as comorbidity with a score of 0.7, and the relation between Depression and Sertraline as treatment, because the drug prescription for depression is in some cases sertraline.

Each entity has a score (i.e. Anxiety—0.9) showing its similarity to the sum of the documents in the retrieved set of documents. 1 indicates an identical term in all the relevant documents The labels are available due to previous annotation of SNOMED by the clinician with the risks, risk factors and treatments, using the terms collector or another module. For example, a link between two risks is labelled with "comorbidity", a link between a risk and a risk factor is labelled with "risk factor" and a link between a treatment and a risk or risk factor is labelled "treatment".

Figure 8:
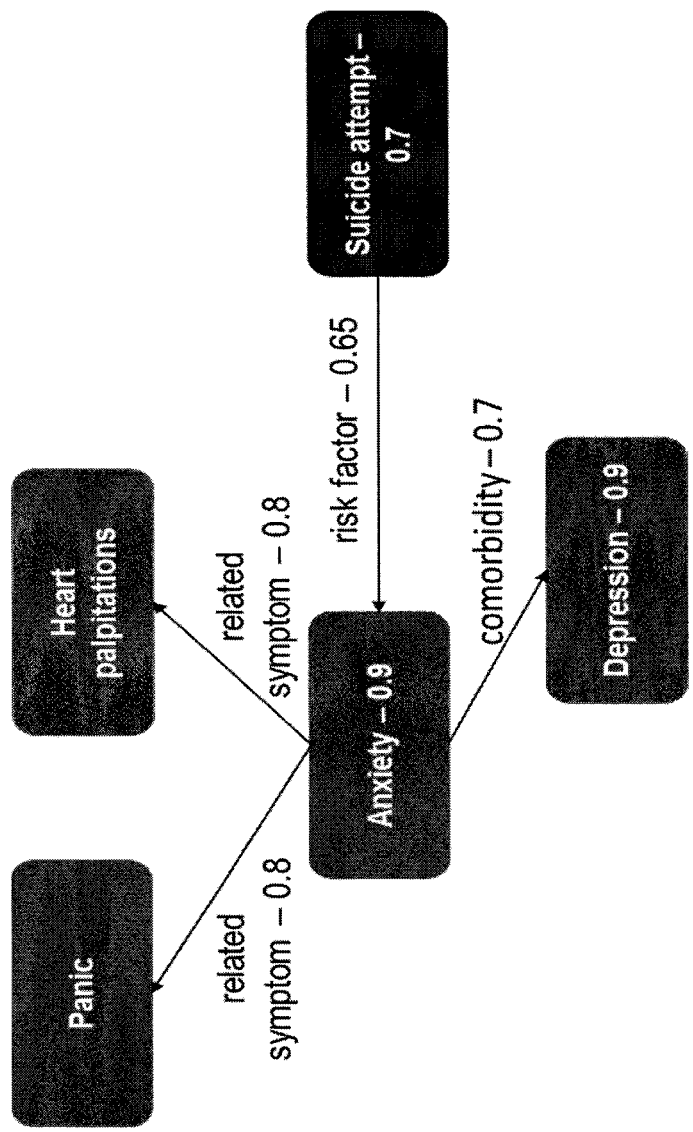
FIG. 8 is an illustration of a patient risk graph.

FIG. 8 shows a patient risk graph, which has combined information about heart palpitations and panic in the PCO with the part of the risk knowledge graph shown in FIG. 7.

Here, the PCO information has been combined with the general derived risk information to give a picture of risks for the individual, which can be, for example, displayed to the user with a GUI.

Figure 9:
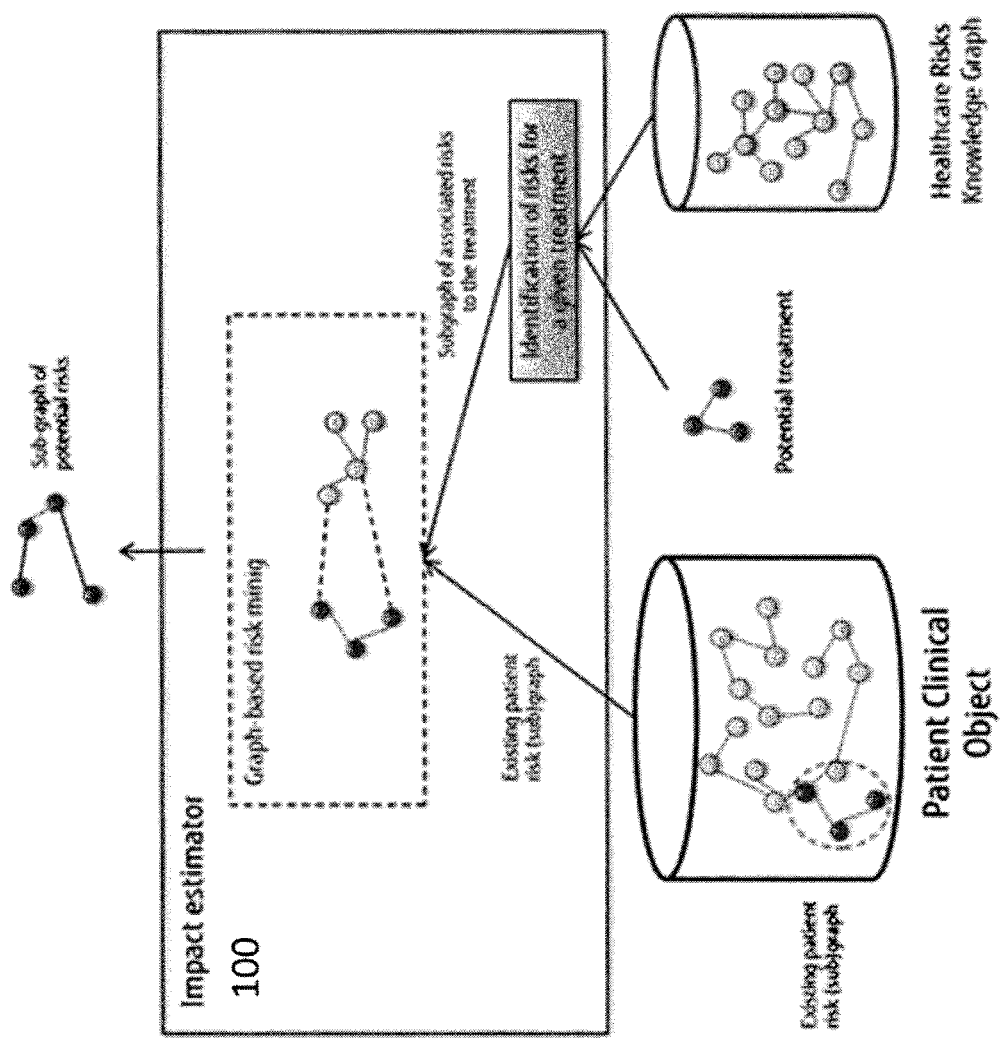
FIG. 9 is a block diagram of impact estimator components in an embodiment of the invention.

A further embodiment incorporates a treatment impact estimator as well as the patient risk graph predictor. Other components remain unchanged and the reader is referred to the previous description thereof. The impact estimator is shown in FIG. 9.

Impact Estimator 100

The module takes as input the associated risks of a particular patient (derived as explained above), and a potential treatment for such patient. The module produces as a result a subgraph of potential risks along with their scores that the patient would have if the clinicians apply the potential treatment.

The potential treatment is related to and affects diagnoses, drug prescription, and future visits. The module takes the treatment related information, e.g., diagnoses, drug prescription, and future visits and search on the Risk Knowledge Graph to collect potential associated risks to the new "status" of the patient, after the application of the treatment. Once the potential associated risks are identified, the module predicts if these risks would affect current patient risks and if so, how.

FIG. 9 depicts the flow of the process.

In a nutshell this module has two main tasks

Identification of risks for a given treatment, in which the module extracts the factors associated with a given treatment, and looks for the risks (of the extracted factors) in the Healthcare Risks Knowledge Graph. Here, the relevant section of the graph around the treatment is selected, for example by including the terms (nodes) that are directly linked to the treatment in the graph, or also including more nodes, for instance the neighbour and the next node(s) along the path.

Graph-based risk assessment and mining, in which the module takes as input the two subgraphs of (1) existing patient risk in the PCO, and (2) associated risks to a given treatment; and performs graph analysis to obtain the potential risks for the patient and given treatment.

The key point here is that the patient risk subgraph can be obtained without any reference to a particular treatment, for example using the symptoms. On the other hand the treatment subgraph can be extracted from the general health risk graph that can contain risks that have not yet being identified for this patient. After the two subgraphs are analysed together the impact graph is created as the result of this join between the treatment graph and the patient graph.

Figure 10:
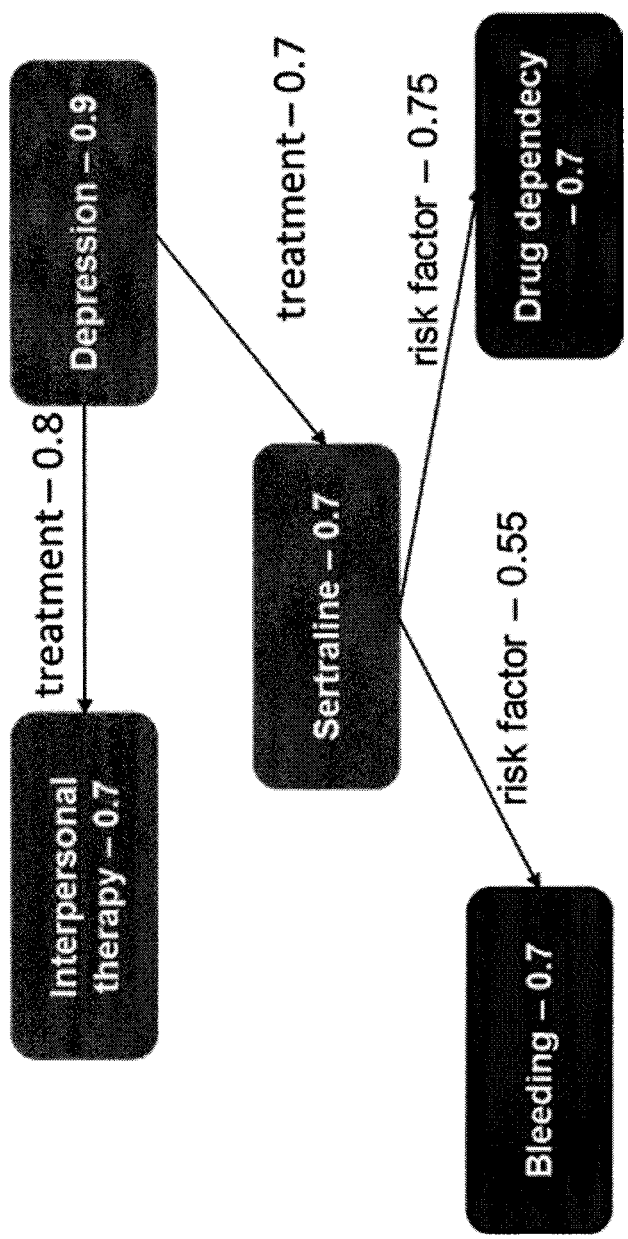
FIG. 10 is an illustration of a treatment subgraph.
Figure 11:
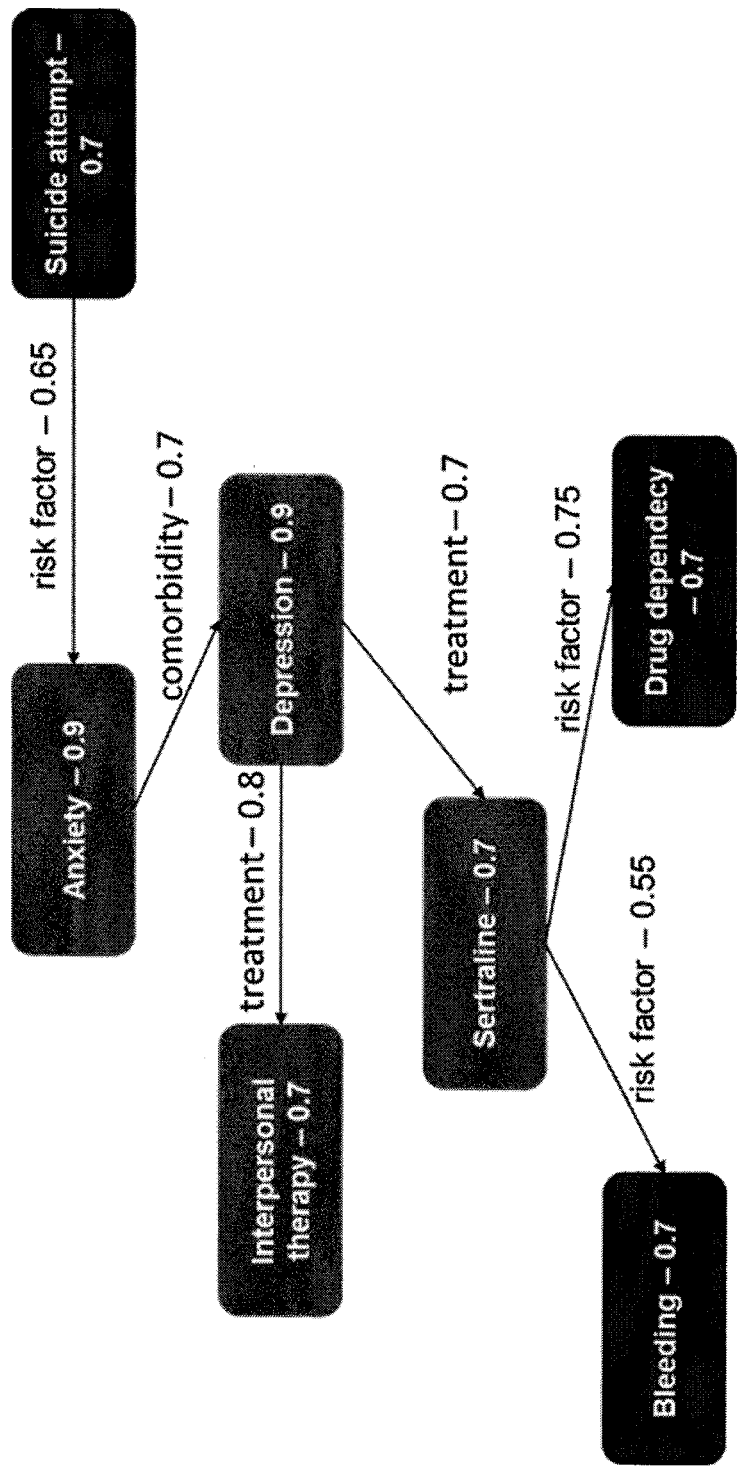
FIG. 11 is an illustration of a graph showing impact of a treatment.

FIGS. 10 and 11 illustrate the patient treatment subgraph and the potential impact of the treatment. The patient risk graph (FIG. 8) is a part of the PCO which has been supplemented using the healthcare risk graph to include risk information. It is therefore relevant to the treatment. The potential treatment is included in the treatment graph example shown in FIG. 10 as Sertraline. This graph has retained the scoring of entities and/or links from the originally from the healthcare risk graph).

The potential impact graph shown in FIG. 11 includes the nodes from the patient treatment subgraph and the healthcare treatment subgraph including at least one intersection node which is a term that was present in both graphs. It also retains the scoring, which can be useful information for the clinician.

Figure 12:
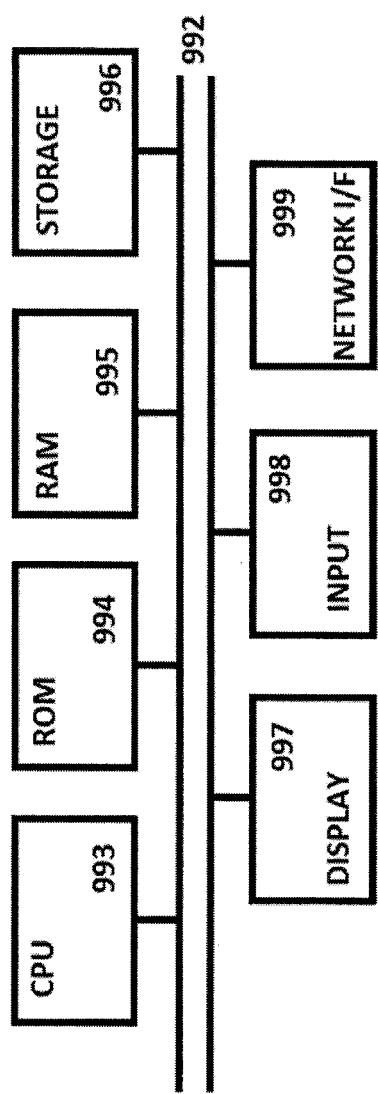
FIG. 12 is a diagram of suitable hardware for implementation of invention embodiments.

FIG. 12 is a block diagram of a computing device, such as a data storage server, which embodies the present invention, and which may be used to implement a method of an embodiment. The computing device comprises a computer processing unit (CPU) 993, memory, such as Random Access Memory (RAM) 995, and storage, such as a hard disk, 996. Optionally, the computing device also includes a network interface 999 for communication with other such computing devices of embodiments. For example, an embodiment may be composed of a network of such computing devices. Optionally, the computing device also includes Read Only Memory 994, one or more input mechanisms such as keyboard and mouse 998, and a display unit such as one or more monitors 997. The components are connectable to one another via a bus 992.

The CPU 993 is configured to control the computing device and execute processing operations. The RAM 995 stores data being read and written by the CPU 993. The storage unit 996 may be, for example, a non-volatile storage unit, and is configured to store data.

The display unit 997 displays a representation of data stored by the computing device and displays a cursor and dialog boxes and screens enabling interaction between a user and the programs and data stored on the computing device. The input mechanisms 998 enable a user to input data and instructions to the computing device.

The network interface (network I/F) 999 is connected to a network, such as the Internet, and is connectable to other such computing devices via the network. The network I/F 999 controls data input/output from/to other apparatus via the network.

Other peripheral devices such as microphone, speakers, printer, power supply unit, fan, case, scanner, trackerball etc may be included in the computing device.

Methods embodying the present invention may be carried out on a computing device such as that illustrated in FIG. 12. Such a computing device need not have every component illustrated in FIG. 12, and may be composed of a subset of those components. A method embodying the present invention may be carried out by a single computing device in communication with one or more data storage servers via a network. The computing device may be a data storage itself storing at least a portion of the data graph. A method embodying the present invention may be carried out by a plurality of computing devices operating in cooperation with one another. One or more of the plurality of computing devices may be a data storage server storing at least a portion of the data graph.

Although a few embodiments have been shown and described, it would be appreciated by those skilled in the art that changes may be made in these embodiments without departing from the principles and spirit of the invention, the scope of which is defined in the claims and their equivalents.

The invention claimed is:

1. A system comprising:
    a healthcare knowledge data input interface to interface with databases of open data and databases of knowledge data in form of risk-related terms relating to a risk;
    at least one processor to cause the system to implement,
        a healthcare risk engine to generate a healthcare risk knowledge graph represented in at least one memory in form of linked data nodes from the databases of open data by retrieving documents from the databases of open data using the risk-related terms and extracting data nodes from the linked data nodes that store entities from the documents corresponding to the risk-related terms and forming links between the extracted data nodes to link the entities;
    a patient risk graph prediction module to combine information in a Patient Clinical Object (PCO) graph obtained from a historical clinical data graph represented in the at least one memory in form of linked data nodes centered on a specific patient, with the entities in the healthcare risk knowledge graph to generate a specific patient risk graph to represent predicted risks for the specific patient in the at least one memory in form of linked data nodes by,
    matching an item of information from the linked data nodes in the PCO graph with a corresponding entity in the linked data nodes in the healthcare risk knowledge graph, and
    forming a data node corresponding to the matched item from the PCO graph to be linked around a data node storing the corresponding entity in the healthcare risk knowledge graph, to form the specific patient risk graph;
    an impact estimator module to estimate an impact of a potential treatment by taking the potential treatment and adjacent data nodes corresponding to the treatment from the linked data nodes of the healthcare risk knowledge graph to form a healthcare treatment subgraph of linked data nodes and finding a corresponding entity and adjacent nodes in the linked data nodes of the specific patient risk graph to form a specific patient treatment subgraph of linked data nodes, and providing an impact graph of linked data nodes by combining the linked data nodes of the specific patient treatment subgraph and the healthcare treatment subgraph and retaining resultant linked data nodes as the impact graph of data nodes; and
    a graphical user interface to display a visual graph representation of the data nodes of the impact graph to display information indicating a potential impact of the potential treatment for the specific patient.

2. A system according to claim 1,
wherein the PCO graph is an aggregation of clinical entities that encapsulates items of information about the specific patient, and
wherein the PCO graph contains the historical clinical information with information about the specific patient linked to the specific patient by categories including any one or combination of categories of diagnosis, symptom, treatment, hospital visit and prescription.

3. A system according to claim 1, wherein the risk-related terms include terms related to risks in form of potential diseases, terms related to risk factors that increase the likelihood of disease and terms related to treatments of a medical condition.

4. A system according to claim 1, wherein the healthcare risk engine comprises:
a risk related terms collector to accept input of the risk-related terms;
a medical entity reconciliator, to standardise and expand the risk-related terms to include synonyms and equivalent terms using a standardised vocabulary of terms;
a topic detector and tagger, to retrieve a set of documents linked to the expanded terms from a medical document database;
a named entity recognition, resolution and disambiguation (NERD) module to extract entities from the documents, each document of the documents with a score and each aligned to the standardised vocabulary; and
a relation extractor to score relations between the entities based on co-occurrence of two entities in the documents in the retrieved documents; wherein
the healthcare risks extraction system is arranged to generate a risk knowledge graph storing the entities and the scored relations of the entities.

5. A system according to claim 1, wherein
the patient risk graph prediction module is a meta-predictor to perform the matching and which is arranged to use the PCO graph in two or more of predictors to produce corresponding respective specific patient risk subgraphs from the healthcare risk knowledge graph, the two or more predictors including:
a diagnosis-based predictor to provide a specific patient risk subgraph based on previous diagnoses,
a drug-based predictor to provide a specific patient risk subgraph based on previous drugs taken by the patient,
a symptom-based predictor to provide a specific patient risk subgraph based on previous symptoms of the patient, and
a treatment-based predictor to provide a specific patient risk subgraph based on treatments the patient is receiving; and wherein
the meta predictor is to indicate predictions by organizing and processing the corresponding respective specific patient risk subgraphs produced by the two or more predictors into the specific patient risk graph.

6. A system according to claim 1, wherein
the impact estimator module takes any nodes matching a healthcare treatment subgraph node and nodes within 1 or 2 or 3 links from the matching node to form the specific patient treatment subgraph.

7. A system according to claim 1, wherein
the impact estimator module takes the entity for the potential treatment from the healthcare risk knowledge graph, and includes further nodes including at least one entity in a risk or risk factor category to form the healthcare treatment subgraph.

8. A system according to claim 1, wherein
the impact estimator module takes the entity for the potential treatment, and includes the risks and/or risk factors within 2 or 3 links from the entity to form the healthcare treatment subgraph.

9. A system according to claim 1, wherein
the impact estimator module takes the entity for the treatment, the risks and/or risk factors within 2 or 3 links from the entity and includes 2 or 3 further links starting from each risk to form the healthcare treatment subgraph.

10. A system according to claim 1, further comprising a translation module to accept a term in one language and translate it into the equivalent in a language of a standardised vocabulary.

11. A computer-implemented method to display information indicating a potential impact of a potential treatment for a specific patient, the method comprising:
by at least one processor,
generating a healthcare risk knowledge graph represented in at least one memory in form of linked data nodes from databases of open data by retrieving documents from the databases of open data using risk-related terms from knowledge databases, and extracting data nodes from the linked data nodes that store entities from the documents corresponding to the risk-related terms and forming links between the extracted data nodes to link the entities;
combining information in a Patient Clinical Object (PCO) graph obtained from a historical clinical data as a graph represented in the at least one memory in form of linked data nodes centered on a specific patient, with the entities in the healthcare risk knowledge graph to generate a specific patient risk graph to represent predicted risks for the specific patient in the at least one memory in form of linked data nodes by,
matching an item of information from the linked data nodes in the PCO graph with a corresponding entity in the linked data nodes in the healthcare risk knowledge graph, and
forming a data node corresponding to the matched item from the PCO graph to be linked around a data node storing the corresponding entity in the healthcare risk knowledge graph, to form the specific patient risk graph;
estimating an impact of a potential treatment by taking the potential treatment and adjacent data nodes corresponding to the treatment from the linked data nodes of the healthcare risk knowledge graph to form a healthcare treatment subgraph of linked data nodes and finding a corresponding entity and adjacent nodes in the linked data nodes of the specific patient risk graph to form a specific patient treatment subgraph of linked data nodes, and providing an impact graph of linked data nodes by combining the linked data nodes of the specific patient treatment subgraph and the healthcare treatment subgraph and retaining resultant linked data nodes as the impact graph of data nodes; and
displaying a graphical user interface on a display to display a visual graph representation of the data nodes of the impact graph to display information indicating a potential impact of the potential treatment for the specific patient.

12. A non-transitory computer-readable medium storing a computer program which when executed on a computer performs a process to display information indicating a potential impact of a potential treatment for a specific patient, the process comprising:

generating a healthcare risk knowledge graph represented in at least one memory in form of linked data nodes from databases of open data by retrieving documents from the databases of open data using risk-related terms from knowledge databases, and extracting data nodes from the linked data nodes that store entities from the documents corresponding to the risk-related terms and forming links between the extracted data nodes to link the entities;

combining information in a Patient Clinical Object (PCO) graph obtained from a historical clinical data as a graph represented in the at least one memory in form of linked data nodes centered on a specific patient, with the entities in the healthcare risk knowledge graph to generate a specific patient risk graph to represent predicted risks for the specific patient in the at least one memory in form of linked data nodes by, matching an item of information from the linked data nodes in the PCO graph with a corresponding entity in the linked data nodes in the healthcare risk knowledge graph, and forming a data node corresponding to the matched item from the PCO graph to be linked around a data node storing the corresponding entity in the healthcare risk knowledge graph, to form the specific patient risk graph;

estimating an impact of a potential treatment by taking the potential treatment and adjacent data nodes corresponding to the treatment from the linked data nodes of the healthcare risk knowledge graph to form a healthcare treatment subgraph of linked data nodes and finding a corresponding entity and adjacent nodes in the linked data nodes of the specific patient risk graph to form a specific patient treatment subgraph of linked data nodes, and providing an impact graph of linked data nodes by combining the linked data nodes of the specific patient treatment subgraph and the healthcare treatment subgraph and retaining resultant inked data nodes as the impact graph of data nodes; and displaying a graphical user interface on a display to display a visual graph representation of the data nodes of the impact graph to display information indicating a potential impact of the potential treatment for the specific patient.

* * * * *